United States Patent [19]

Redmond et al.

[11] 4,364,395
[45] Dec. 21, 1982

[54] LOW PROFILE SHUNT SYSTEM

[75] Inventors: Russell J. Redmond, Santa Barbara; Donald L. Hannula, Goleta, both of Calif.

[73] Assignee: American Heyer-Schulte Corporation, Goleta, Calif.

[21] Appl. No.: 279,107

[22] Filed: Jun. 30, 1981

[51] Int. Cl.³ ............................................. A61M 27/00
[52] U.S. Cl. ...................................... 604/10; 137/510
[58] Field of Search ....................... 128/350 V, 350 R; 137/510

[56] References Cited

U.S. PATENT DOCUMENTS

| | | | |
|---|---|---|---|
| 3,111,125 | 11/1963 | Schulte | 128/350 V X |
| 3,503,402 | 3/1970 | Schulte | 128/350 |
| 3,566,913 | 3/1971 | Parthe, Jr. | 137/510 X |
| 3,595,240 | 7/1971 | Mishler | 128/350 X |
| 3,756,243 | 9/1973 | Schulte | 128/350 V |
| 3,768,508 | 10/1973 | Schulte | 128/350 V X |
| 3,769,982 | 11/1973 | Schulte | 128/350 V |
| 3,827,439 | 8/1974 | Schulte et al. | 128/350 V |
| 3,901,245 | 8/1975 | Spitz et al. | 128/350 |
| 3,991,768 | 11/1976 | Portnoy | 128/350 V |
| 3,999,553 | 12/1976 | Spitz et al. | 128/350 |

Primary Examiner—Stephen C. Pellegrino
Attorney, Agent, or Firm—Roger A. Williams

[57] ABSTRACT

A shunt system for implantation in the body which can be used for transferring cerebrospinal fluid is disclosed. The shunt system comprises a body having an upper and lower surface and a distal and proximal end. The body includes a central cavity opening through the upper surface at a first and second port. A proximal fluid flow channel extends through the proximal end of the body and opens at a third port on the upper surface. A distal fluid flow channel extends through the distal end of the body and opens at a fourth port on the upper surface. A resilient dome comprised of a self-sealing material is attached to and extends over the upper surface of the body. A first portion of the resilient dome extends over the first and third ports on the upper surface defining a first chamber. The first portion of the resilient dome cooperates upon flexing with the third port to occlude the third port. A second portion of the resilient dome extends over the second and fourth ports on the upper surface defining a second chamber. The second portion of the resilient dome cooperates upon flexing with the fourth port to occlude the fourth port.

17 Claims, 5 Drawing Figures

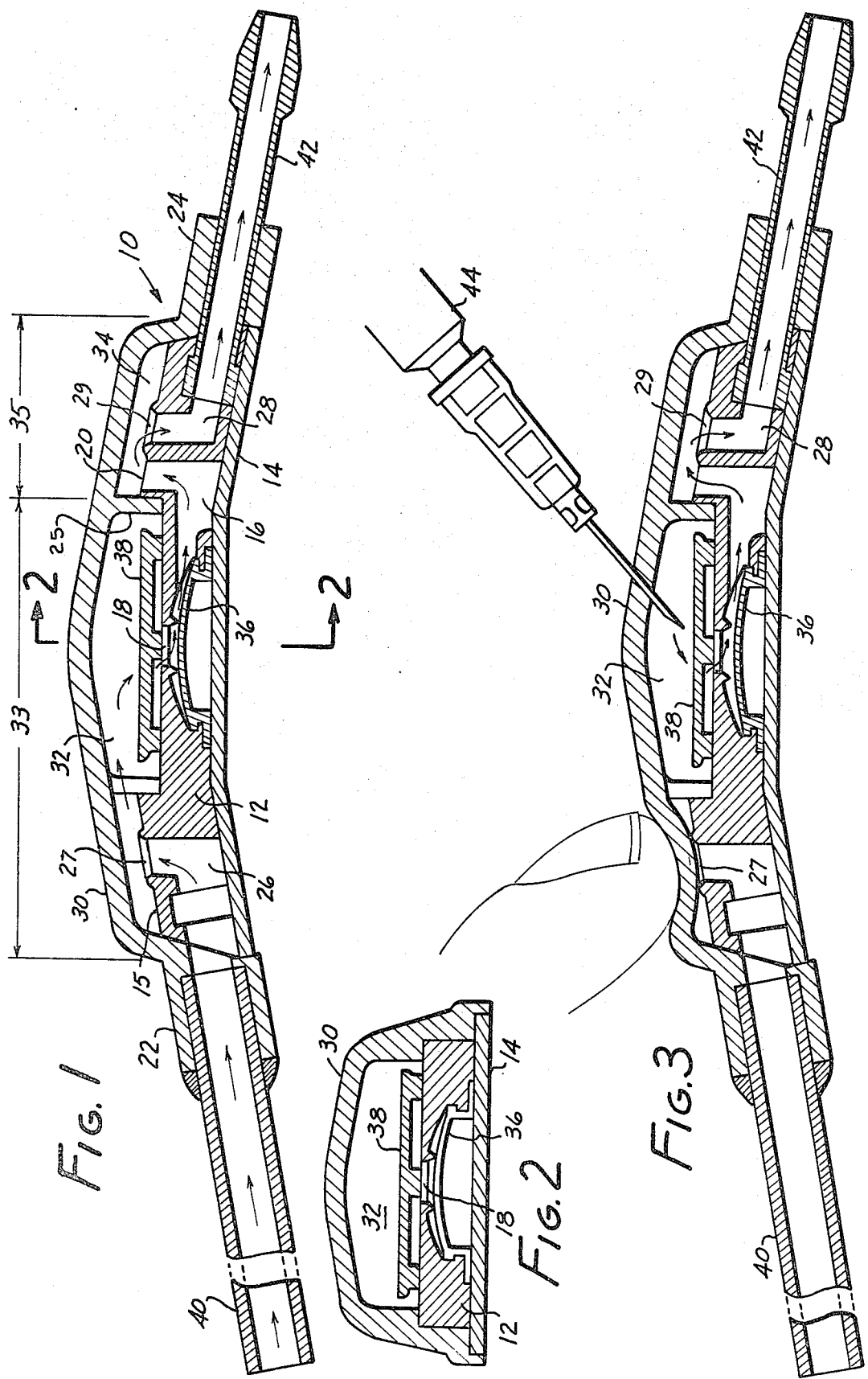

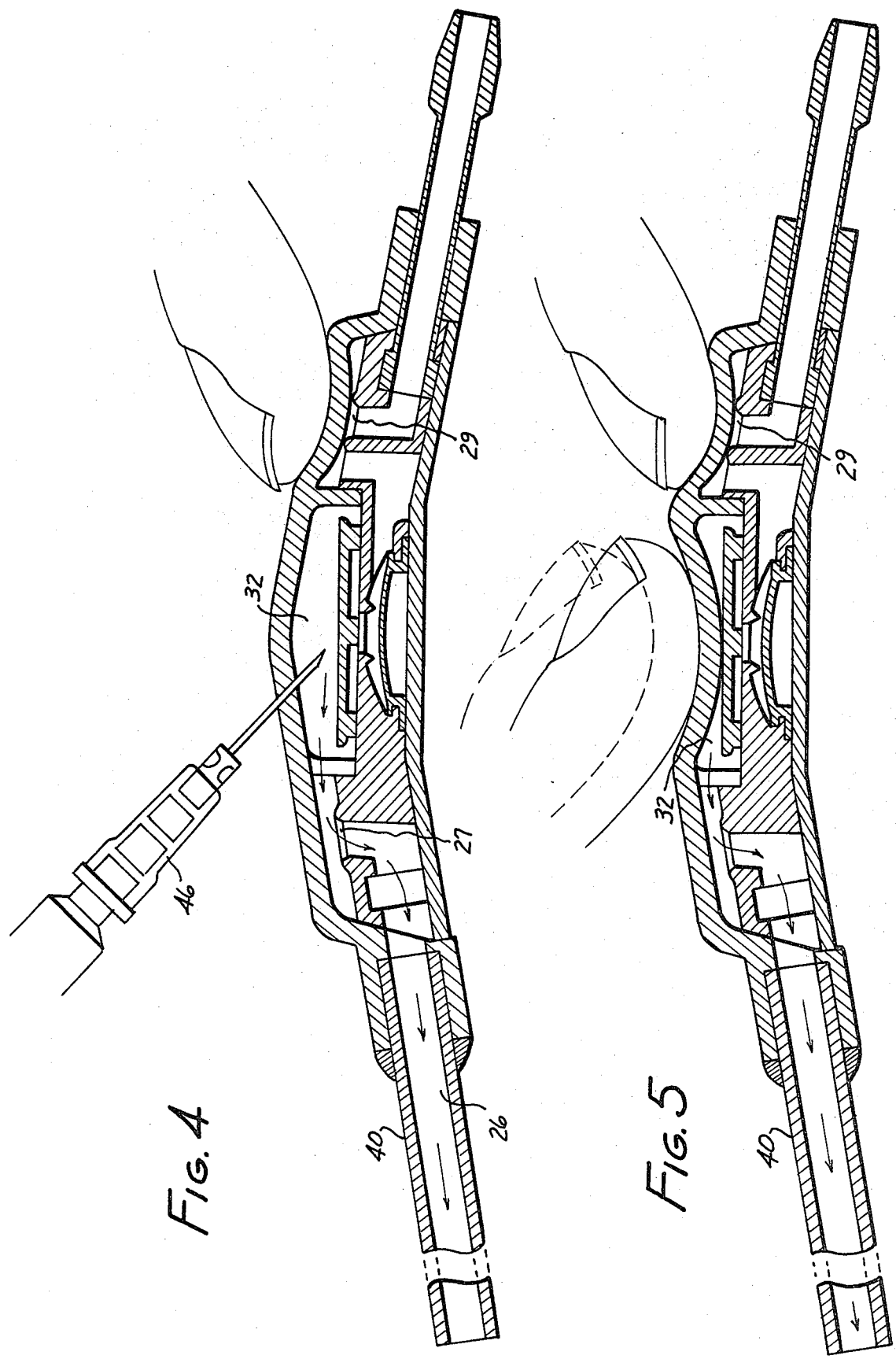

LOW PROFILE SHUNT SYSTEM

BACKGROUND OF THE INVENTION

The invention herein relates to a low profile shunt system for implanting in the body to enable the transfer of body fluids.

Shunt systems for drainage of unwanted body fluids from one region of the body to another region are generally known. A well-known usage of such shunt systems is in the treatment of hydrocephalus, wherein excess cerebrospinal fluid (CSF) is drained from the ventricles of the brain to either the right atrium or the peritoneum. A known example of such a system is shown in Rudolf R. Schulte, U.S. Pat. No. 3,111,125, issued Nov. 19, 1963 entitled "Drainage Device." Another such device is disclosed in Alan J. Mishler, U.S. Pat. No. 3,595,240 and still another system is disclosed in U.S. Pat. No. 3,827,439 to Rudolf R. Schulte and Harold D. Portnoy.

The above described devices are often implanted under the skin and connected to a ventricle drainage tube in the brain. The devices are also attached to a catheter which is inserted into the right atrium of the heart or into the peritoneum. After implantation and use over extended time periods, such devices tend to become clogged in certain individuals. Such clogging tends to occur at the catheter or passageway from the ventricle of the brain leading into inner chambers of the devices due to foreign materials which collect in the narrow tubular passageways of the devices and at the openings in such passageways to the drain. Consequently, it is often necessary to perform second or subsequent operations on an individual to remove devices which have become clogged. Some of the devices provide means for flushing the devices. However, usually the flushing devices have a relatively high profile such that long periods of implant are difficult to tolerate by the patient due to skin erosion, such as can occur with premature infants, pediatric patients and older patients. In addition, the flushing of some of such devices is difficult and sometimes futile. The inconvenience, cost, and physical and psychological problems involved in performing the additional operations and in using the relatively high profile shunting systems are considerable and undesirable.

SUMMARY OF THE INVENTION

The shunt system herein provides a low profile implantable shunt system having utility in the treatment of hydrocephalus. The shunt system comprises a body having an upper and lower surface and a distal and proximal end. The body includes a central cavity which opens through the upper surface at a first port and a second port.

Two fluid flow channels extend through the body independently of the central cavity. One of the fluid flow channels is referred to herein as a proximal fluid flow channel extending through the proximal end of the body and opening at a third port provided on the upper surface. The other fluid flow channel is referred to as a distal fluid flow channel which extends through the distal end of the body and opens at a fourth port provided on the upper surface.

A resiliently flexible dome is attached to and extends over the upper surface of the body. A first portion of the resilient dome extends over the first and third ports provided on the upper surface. The first portion and upper surface define a first chamber within the shunt system. The first portion of the resilient dome can be compressed upon application of a force to cooperate with the third port on the upper surface to occlude the third port. Upon release of the pressure the first portion recovers, thereby opening the third port to fluid flow. A second portion of the resilient dome extends over the second and fourth ports provided on the upper surface of the body. The second portion and upper surface define a second independent chamber separated from the first chamber by an interior wall. The second portion of the resilient dome cooperates upon flexing and exertion of a force against it with the fourth port to occlude the fourth port. Upon releasing the force, the second portion of the resilient dome recovers, thereby opening the fourth port to fluid flow.

A diaphragm valve is positioned within the central cavity of the body. The diaphragm valve cooperates with the first port which acts as a valve seat. The cooperative action of the diaphragm valve and first port provide opening and closing of the port to fluid flow. A needle guard can be provided in the first chamber positioned above the diaphragm valve. The needle guard protects the diaphragm valve from puncture when a needle is inserted into the first chamber.

In operation, the shunt system is implanted within the body with the proximal end and proximal fluid flow conduit of the shunt system in fluid flow communication with a ventricular drain placed in the ventricles of the brain of the patient. The cerebrospinal fluid flows into and through the drain, through tubing connecting the drain to the shunt system and into the proximal fluid flow channel. The CSF flows from the proximal fluid flow channel into the first chamber. When a sufficient pressure has been established in the first chamber, the resistance force of the diaphragm valve is overcome and the diaphragm valve compresses, opening the first port to fluid flow. The CSF flows from the first chamber into the central cavity. The CSF flows through the central cavity and through the second opening into the second chamber. From the second chamber, the CSF flows through the fourth port and into the distal fluid flow channel. At the distal end of the shunt system, there is a connector connecting the shunt system to suitable tubing, which tubing is also connected to a drain tube positioned in the right atrium of the heart or the peritoneum. The CSF thusly flows from the distal fluid flow channel to the heart or peritoneum.

BRIEF DESCRIPTION OF THE DRAWINGS

FIG. 1 is a side elevational view in section of an embodiment of the shunt system herein;

FIG. 2 is an enlarged cross section taken at line 6—6 of FIG. 1;

FIG. 3 is a side elevational view in cross section of the shunt system illustrating a technique for injection for distal flushing;

FIG. 4 is a side elevational view in cross section of the shunt system illustrating a technique for injection for proximal flushing; and FIG. 5 is a side elevational view in cross section illustrating a technique for proximal pumping.

DETAILED DESCRIPTION OF THE INVENTION

With reference to FIG. 1, there is shown a working embodiment of a shunt system which can be used to drain or assist in the transfer of fluids from one portion of the human body to another. The shunting system herein can be used in diverting fluid from an area of higher pressure to an area of lower pressure. In particular, the shunt system shown in FIG. 1 has utility in the transfer of cereborspinal fluid from the ventricles of the brain to either the right atrium of the heart or the peritoneum. The system can also be flushed either proximally or distally to prevent or dislodge blockages which occur either proximally or distally of the system. The shunt system provides such features in a relatively low profile device.

With regard to FIG. 1, the shunt system 10 comprises a body 12 having a base 14 and an upper surface 15. The base 14 is essentially flat, but is shaped to approximate the contours of the human head, and in particular, the head of an infant. Thus, when implanted, the shunt system 10 rests with its base 14 lying against the head of the recipient.

Within the body 12 of the shunt system, there is a central cavity 16. The central cavity 16 is centrally located within the body and is open through a first port 18 and a second port 20 which both open and are provided on the upper surfaces 15.

The body of the shunt system is described herein with regard to a proximal end 22 and a distal end 24. The ends of the body are described as being proximal and distal with regard to the general liquid flow path through the shunt system. That is, in the normal functioning of the shunt system fluid flow is from the proximal end 22 to the distal end 24. For example, when the device is utilized as a shunt system for the treatment of hydrocephalus, the proximal end 22 is connected to tubing leading to a drainage tube in the ventricles of the brain. The distal end 24 of the shunt system is connected to suitable tubing leading to either an arterial or peritoneal catheter positioned in the heart or peritoneum.

Extending through the proximal end of the body is a proximal fluid flow passageway or channel 26. The proximal fluid flow channel extends through the proximal end and opens through the upper surface 15 at a third port 27 provided on the upper surface.

A distal fluid flow passageway or channel 28 extends through the distal end of the body. The distal fluid flow channel opens through the upper surface 15 of the body through a fourth port 29 provided on the upper surface.

A resilient dome 30 is sealably fastened to the body 12. The resilient dome is constructed of a flexible self-sealing material, such as a silicone elastomer. The shunt system can be conveniently made of silicone elastomer. The resilient dome is flexible and can be pressed against the body 12 of the shunt system when a force is applied to the resilient dome. In addition, the resilient dome is capable of sealing upon itself when punctured with a needle, such as the needle on a syringe. In a working embodiment, the resilient dome was constructed of a silicone rubber which was self-sealing when penetrated by a 25 gauge or smaller needle.

The resilient dome extends over the upper surface of the body. A first portion 33 of the resilient dome is spaced apart from the upper surface forming a first chamber 32 between the upper surface and resilient dome. The first port and the third port are provided on the upper surface within the first chamber. The first chamber 32 is sometimes herein referred to as a reservoir chamber. A second portion 35 of the resilient dome extends over a portion of the upper surface forming a second chamber 34. The second chamber 34 is independent and separated from the first cahmber 32 by an intervening wall 25. The portion of the upper surface 15 lying within the second chamber includes a portion of the upper surface on which is provided the second and fourth ports.

A diaphragm valve 36 is fastened and positioned within the central cavity 16. The diaphragm valve 36 cooperates with the first port 18 which acts as a valve seat. In the cooperative working of the diaphragm valve and valve seat, the first port 18 is either open or closed to the flow of fluid from the first chamber to the central cavity. When the diaphragm valve is in the open position, the flow of fluid is through the first port 18 and over the surface of the diaphragm valve. The diaphragm valve also functions as a check valve to prevent or inhibit the back flow of fluid from the central cavity into the first chamber.

The diaphragm valve can be made or selected to provide opening of the first port at differing levels of pressure within the first chamber. That is, by changing the diaphragm valve the shunt system can be varied to operate at different pressures as may be required in particular patients. The pressure resistance of the diaphragm valve can be changed by changing the physical characteristics of the diaphragm valve, such as thickness, or providing apertures through the diaphragm valve. In working embodiments, three separate shunt systems were prepared wherein the three embodiments had a closing pressure in millimeters of water of 5 through 50, 51 through 110, and 111 through 180 respectively. For the three embodiments at a flow of 5 milliliters per hour, the embodiments exhibited a minimum differential pressure of 5 mm. water, 51 mm. water, and 111 mm. of water respectively. For a flow of 50 ml. per hour, the three embodiments exhibited maximum differential pressures in millimeters of water of 75, 140, and 220 respectively.

Positioned within the first chamber on the upper surface 15 over the first opening 18 can be a needle guard 38. The needle guard can be made of a relatively hard and durable material, such as polypropylene, which can resist penetration by a needle. A syringe is utilized to flush the shunt system by penetrating the resilient dome 30. When a needle is used to flush the shunt system, puncture of the diaphragm is avoided by including a needle guard 38 within the first chamber over the diaphragm valve.

The shunt system herein can also include a proximal tube 40 integrally connected to the body of the shunt system. That is, the proximal tube 40 can be adhesively or thermally bonded to the body. The proximal tube 40 can be constructed of any suitable material compatible with the human body and capable of being bonded to the body of the shunt system. Alternatively, a proximal connecter integrally connected to the body can be provided for attaching a ventricular drain to the body.

At the distal end 24 of the body of the shunt system can be a distal connector 42 integrally connected to the body. The distal connector 42 can be constructed of any suitable material, such as available plastics compatible with the body. The distal connector 42 provides a location for attachment of a catheter lead which can be connected to the distal connector and secured by ligatures.

The shunt system herein is constructed and designed to provide a low profile shunt system. In the working embodiments, the shunt system was constructed having a base with an overall length of 23 millimeters. The height of the shunt system at its greatest height, from the base to the top of the resilient dome, was 5 mm. The base had a width at its widest point of about 12 mm. The proximal tube had an outside diameter of 2.1 mm. and an inside diameter of 1.2 mm. The length of the proximal tube was designed to be 15 centimeters which was sufficient to lead from the implantation site for the shunt system to a drain positioned in the ventricles of the brain.

In normal operations, such as in use for the treatment of hydrocephalus, CSF drains from the brain to the shunt system and through the proximal fluid flow channel into the first chamber or reservoir chamber. The CSF collects in the reservoir chamber until a sufficient fluid pressure is achieved to overcome the diaphragm valve. When sufficient pressure develops, the CSF flows through the first port and over the diaphragm valve into the central cavity. The CSF flows through the central cavity, second chamber and distal fluid flow channel into the lead of a drainage catheter attached to the connector.

The shunt system herein provides both distal and proximal flushing capabilities. Fluids can be selectively flushed in the proximal or distal direction by injecting the fluid through the self-sealing wall of the resilient dome into the first chamber. To selectively flush either distally or proximally, the third or fourth port is closed. With regard to distal flushing of the shunt system, a technique is illustrated in FIG. 3. A syringe 44 containing a suitable fluid for flushing is inserted through the wall of the resilient dome 30. The needle of the syringe is inserted through the wall into the first chamber 32. The needle guard 38 prevents rupture of the diaphragm valve 36. After insertion of the needle into the first chamber, pressure is applied to the wall of the resilient dome to press the wall against the third port 27. The wall cooperates with the third port 27 to occlude the third port and prevent fluid flow therethrough. As the syringe is activated to inject fluid into the first chamber, the fluid flows through a pathway which is in a distal direction. That is, the fluid flows into the first chamber through the first port past the diaphragm valve, in and through the central cavity and into the second chamber. From the second chamber, the fliud flows through the fourth port and through the distal fluid flow channel. Normal functioning of the shunt system can be resumed by removing the pressure occluding the third port 27 and withdrawing the needle, whereupon the flexible wall self-seals, closing the injection site.

With regard to FIG. 4, a similar technique is illustrated for proximal flushing of the shunt system. A needle of a syringe 46 is inserted through the self-sealing and flexible wall of the resilient dome such that the needle penetrates into the first chamber 32. A pressure is exerted on the second portion 35 of the resilient dome over the fourth port 29. A pressure is exerted sufficient to contact the flexible wall with the fourth port 29 to occlude the fourth port to fluid flow. As the fluid from the syringe is injected into the first chamber 32, the only available flow path for the fluid is in a proximal direction. That is, the fluid flows from the first chamber through the third port 27 and through the proximal fluid flow channel 26. Normal functioning of the shunt system is resumed by releasing the pressure on the resilient dome and withdrawing the needle.

The first chamber of the shunt system herein functions as a reservoir chamber. That is, the cerebrospinal fluid is stored in the first chamber until a sufficient pressure is achieved to open the diaphragm valve. As the shunt system herein has a capacity for storing the CSF, there is no need for utilizing a separate reservoir chamber. Prior to the buildup of sufficient pressure in the first chamber to overcome the diaphragm valve, there can be occasion to pump the CSF present in the first chamber either distally or proximally. For distal pumping of the CSF, the resilient dome can be pressed, such as with one's finger, to exert additional pressure in the CSF, thus overcoming the resistance of the diaphragm valve. If proximal pumping is desired, pressure is exerted on the resilient dome over the second portion 35 to occlude the fourth port 29 as is shown in FIG. 5. Additional pressure is then exerted on the resilient dome over the first chamber. As the distal fluid flow channel is occluded, the CSF present in the first chamber flows proximally through the proximal fluid flow channel.

The base 14 of the body can be reinforced to prevent tear out when the device is anchored to the peritoneum. For example, the base can be reinforced with DACRON (registered trademark of E. I. DuPont de Nemours and Company). The reinforced base can also be impregnated with a material to provide the shunt system with an ability to be located, such as through X-rays. That is, the reinforced sheeting on the base can be impregnated with barium to assist in post-operative location of the shunt system.

We claim:

1. A shunt system for implantation in the body, comprising:
    a body having an upper and lower surface and a distal and proximal end, the body including a central cavity opening through the upper surface at a first and second port, a proximal fluid flow channel extending through the proximal end of the body and opening at a third port on the upper surface, and a distal fluid flow channel extending through the distal end of the body opening at a fourth port on the upper surface;
    a resilient dome attached to and extending over the upper surface of the body, a first portion of the resilient dome extending over the first and third ports on the upper surface defining a first chamber wherein the first portion of the resilient dome upon flexing cooperates with the third port to occlude the third port and wherein a second portion of the resilient dome extends over the second and fourth ports on the upper surface defining a second chamber wherein the second portion of the resilient dome cooperates upon flexing with the fourth port to occlude the fourth port; and
    a diaphragm valve means positioned within the central cavity for cooperating with the first port to open or close the first port to fluid flow between the central cavity and first chamber.

2. A shunt system as recited in claim 1 further comprising a needle guard means within the central cavity for protecting the diaphragm valve means from puncture when a needle is inserted through the resilient dome into the first chamber.

3. A shunt system as recited in claim 1 further comprising tubing means integrally connected to the body at the proximal end in fluid flow communication with the proximal fluid flow channel.

4. A shunt system as recited in claim 1 further comprising a proximal connector means integrally attached to the body for connecting a ventricular drain to the body.

5. A shunt system as recited in claim 1 further comprising a distal connector means for connecting to a drainage catheter, integrally attached to the distal end of the body in fluid flow communication with the distal fluid flow channel.

6. A shunt system as recited in claim 1 wherein the lower surface of the body is substantially flat and contoured to approximate the contours of the human skull.

7. A shunt system as recited in claim 1 having a length from the distal end to the proximal end of about 23 millimeters.

8. A shunt system as recited in claim 1 wherein the height of the shunt system from the lower surface of the body to the resilient dome is about 5 millimeters.

9. A shunt system as recited in claim 1 wherein the resilient dome comprises a self-sealing material.

10. A shunt system for implantation in the body, comprising:

a body having an upper and lower surface and a distal and proximal end, the body including a central cavity opening through the upper surface at a first and second port, a proximal fluid flow channel extending through the proximal end of the body and opening at a third port on the upper surface, and a distal fluid flow channel extending through the distal end of the body opening at a fourth port on the upper surface;

a resilient dome comprised of a self-sealing material attached to and extending over the upper surface of the body, a first portion of the resilient dome extending over the first and third ports on the upper surface defining a first chamber wherein the first portion of the resilient dome upon flexing cooperates with the third port to occlude the third port and wherein a second portion of the resilient dome extends over the second and fourth ports on the upper surface defining a second chamber wherein the second portion of the resilient dome cooperates upon flexing with the fourth port to occlude the fourth port;

a diaphragm valve means positioned within the central cavity for cooperating with the first port to open or close the first port to fluid flow between the central cavity and first chamber;

a needle guard means within the central cavity for protecting the diaphragm valve means from puncture when a needle is inserted through the resilient dome into the first chamber;

tubing means integrally connected to the body at the proximal end in fluid flow communication with the proximal fluid flow channel; and a distal connector means for connecting to a drainage catheter, integrally attached to the distal end of the body in fluid flow communication with the distal fluid flow channel.

11. A shunt system as recited in claim 10 wherein the diaphragm valve means opens the valve seat to fluid flow at a pressure from about 5 to about 50 millimeters of water.

12. A shunt system as recited in claim 10 wherein the diaphragm valve means opens the valve seat to fluid flow pressure from about 51 to about 110 millimeters of water.

13. A shunt system as recited in claim 10 wherein the diaphragm valve means opens the valve seat to fluid flow pressure from about 111 to about 180 millimeters of water.

14. A shunt system as recited in claim 10 further comprising a radiopaque base attached to the lower surface of the body.

15. A shunt system as recited in claim 10 wherein the lower surface of the body is substantially flat and contoured to approximate the contours of the human skull.

16. A shunt system as recited in claim 10 having a length from the distal end to the proximal end of about 23 millimeters.

17. A shunt system as recited in claim 10 wherein the height of the shunt system from the lower surface of the body to the resilient dome is about 5 millimeters.

* * * * *